United States Patent
Bahlmann et al.

(10) Patent No.: US 10,138,209 B2
(45) Date of Patent: Nov. 27, 2018

(54) PROCESS FOR PURIFYING AN IONIC LIQUID

(71) Applicant: Evonik Degussa GmbH, Essen (DE)

(72) Inventors: Matthias Bahlmann, Heiden (DE); Olivier Zehnacker, Dortmund (DE); Markus Lütkehaus, Steinfurt (DE); Benjamin Willy, Düsseldorf (DE); Werner Escher, Neuss (DE); Xinming Wang, Kanagawa-ken (JP); Rolf Schneider, Gründau-Rothenbergen (DE); Christoph Hiller, Dülmen (DE); Stefan Münzner, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/486,300

(22) Filed: Apr. 13, 2017

(65) Prior Publication Data

US 2017/0355681 A1 Dec. 14, 2017

(30) Foreign Application Priority Data

Jun. 14, 2016 (DE) .................. 10 2016 210 481

(51) Int. Cl.
*C07D 233/58* (2006.01)
*C07F 9/141* (2006.01)
*B01D 1/14* (2006.01)

(52) U.S. Cl.
CPC ............. *C07D 233/58* (2013.01); *B01D 1/14* (2013.01); *C07F 9/141* (2013.01)

(58) Field of Classification Search
CPC .......... C07D 233/58; B01D 1/14; C07F 9/141
USPC ...................................... 548/335.1
See application file for complete search history.

(56) References Cited

U.S. PATENT DOCUMENTS

| | | | |
|---|---|---|---|
| 1,882,258 A | 10/1932 | Randel | |
| 2,516,625 A | 7/1950 | Haury | |
| 2,601,673 A | 6/1952 | McMillan et al. | |
| 2,802,344 A | 8/1957 | Witherell | |
| 3,276,217 A | 10/1966 | Bourne et al. | |
| 3,317,654 A | 5/1967 | Johnson et al. | |
| 3,580,759 A | 5/1971 | Albertson et al. | |
| 3,609,087 A | 9/1971 | Chi et al. | |
| 3,927,151 A | 12/1975 | Ishmail | |
| 4,046,719 A | 9/1977 | Stanaback | |
| 4,079,263 A | 3/1978 | Inoue | |
| 4,094,957 A | 6/1978 | Sartori et al. | |
| 4,106,904 A | 8/1978 | Oude Alink et al. | |
| 4,112,051 A | 9/1978 | Sartori et al. | |
| 4,152,900 A | 5/1979 | Chopra et al. | |
| 4,152,901 A | 5/1979 | Munters | |
| 4,201,721 A | 5/1980 | Hallgren | |
| 4,217,238 A | 8/1980 | Sartori et al. | |
| 4,251,494 A | 2/1981 | Say | |
| 4,360,363 A | 11/1982 | Ferrin et al. | |
| 4,405,579 A | 9/1983 | Sartori et al. | |
| 4,405,586 A | 9/1983 | Sartori et al. | |
| 4,466,915 A | 8/1984 | Lai | |
| 4,489,563 A | 12/1984 | Kalina | |
| 4,524,587 A | 6/1985 | Kantor | |
| 4,525,294 A | 6/1985 | Sartori et al. | |
| 4,605,743 A | 8/1986 | Malz et al. | |
| 4,643,000 A | 2/1987 | Rheinfelder | |
| 4,701,530 A | 10/1987 | Swearingen et al. | |
| 4,714,597 A | 12/1987 | Trevino | |
| 4,889,938 A | 12/1989 | Kristen et al. | |
| 5,016,445 A | 5/1991 | Wehr | |
| 5,126,189 A | 6/1992 | Tanny et al. | |
| 5,186,009 A | 2/1993 | Rockenfeller | |
| 5,186,010 A | 2/1993 | Wehr | |
| 5,245,070 A | 9/1993 | Nishikawa | |
| 5,255,534 A | 10/1993 | Ryan | |
| 5,303,565 A | 4/1994 | Pravada | |
| 5,390,509 A | 2/1995 | Rockenfeller et al. | |
| 5,583,270 A | 12/1996 | Nishiguchi | |
| 5,873,260 A | 2/1999 | Linhardt et al. | |
| 6,117,963 A | 9/2000 | Boinowitz et al. | |
| 6,128,917 A | 10/2000 | Riesch et al. | |
| 6,130,347 A | 10/2000 | Julius et al. | |
| 6,155,057 A | 12/2000 | Angell et al. | |
| 6,165,433 A | 12/2000 | Chakravarti et al. | |
| 6,184,433 B1 | 2/2001 | Harada et al. | |
| 6,423,282 B1 | 7/2002 | Araki et al. | |
| 6,475,370 B2 | 11/2002 | Lehmann et al. | |
| 6,672,099 B1 | 1/2004 | Yoshimi et al. | |
| 6,680,047 B2 | 1/2004 | Klaveness et al. | |
| 6,727,015 B1 | 4/2004 | Putter et al. | |
| 7,419,646 B2 | 9/2008 | Cadours et al. | |

(Continued)

FOREIGN PATENT DOCUMENTS

| | | |
|---|---|---|
| CA | 2 817 704 | 5/2012 |
| CN | 1076380 A | 9/1993 |

(Continued)

OTHER PUBLICATIONS

U.S. Appl. No. 15/742,436, filed Jan. 5, 2018, Zehnacker.
Blachly, et al., "Stabilization of Monoethanolmine Solutions in Carbon Dioxide Scrubbers," *J. Chem. Eng. Data* 11(3):401-403 (Jul. 1966).
Call, "Aminoxyle—eine Klasse stabiler," *Pharmazie in unserer Zeit* 3:83-95 (Jan. 1977); with English language translation attached.
Kirchhoff, et al., "Triacetoneamine Derivatives Industrial Applications and Recent Developments," pp. 1-9, Addcon World '99 (Two-Day Conference, Oct. 1999).

(Continued)

*Primary Examiner* — Kristin A Vajda
(74) *Attorney, Agent, or Firm* — Law Office of Michael A. Sanzo, LLC

(57) ABSTRACT

The invention relates to a process for purifying an ionic liquid comprising dialkylimidazolium ions by means of stripping, wherein water vapor is used at a particular temperature. The process according to the invention is characterized in that the decomposition of the ionic liquid is minimized during the procedure of the process.

20 Claims, No Drawings

(56) References Cited

U.S. PATENT DOCUMENTS

| | | |
|---|---|---|
| 7,435,318 B2 | 10/2008 | Arlt et al. |
| 7,638,636 B2 | 12/2009 | Zhou et al. |
| 7,666,813 B2 | 2/2010 | Hoefer et al. |
| 7,754,053 B2 | 7/2010 | Maase |
| 7,827,820 B2 | 11/2010 | Weimer et al. |
| 7,998,714 B2 | 8/2011 | Gellett et al. |
| 8,069,687 B2 | 12/2011 | Jork et al. |
| 8,167,983 B2 | 5/2012 | Seiler et al. |
| 8,277,615 B2 | 10/2012 | Ruffert et al. |
| 8,318,117 B2 | 11/2012 | Lichtfers et al. |
| 8,357,344 B2 | 1/2013 | Bouillon et al. |
| 8,362,095 B2 | 1/2013 | Schwab et al. |
| 8,382,962 B2 | 2/2013 | Massonne et al. |
| 8,470,079 B2 | 6/2013 | Agar et al. |
| 8,500,867 B2 | 8/2013 | Seiler et al. |
| 8,500,892 B2 | 8/2013 | Seiler et al. |
| 8,506,839 B2 | 8/2013 | Shiflett et al. |
| 8,523,978 B2 | 9/2013 | Rojey et al. |
| 8,623,123 B2 | 1/2014 | Seiler et al. |
| 8,696,928 B2 | 4/2014 | Seiler et al. |
| 8,703,451 B2 | 4/2014 | Haas et al. |
| 8,715,521 B2 | 5/2014 | Shiflett et al. |
| 8,784,537 B2 | 7/2014 | Seiler et al. |
| 8,809,576 B2 | 8/2014 | Schraven et al. |
| 8,932,478 B2 | 1/2015 | Seiler et al. |
| 9,221,007 B2 | 12/2015 | Rolker et al. |
| 9,409,122 B2 | 8/2016 | Qi et al. |
| 9,630,140 B2 | 4/2017 | Willy et al. |
| 9,840,473 B1 | 12/2017 | Wang et al. |
| 9,878,285 B2 | 1/2018 | Schraven et al. |
| 2004/0016631 A1 | 1/2004 | Madkour |
| 2004/0133058 A1 | 7/2004 | Arlt et al. |
| 2005/0070717 A1 | 3/2005 | Wasserscheid et al. |
| 2005/0129598 A1 | 6/2005 | Chinn |
| 2005/0164082 A1 | 7/2005 | Kishi et al. |
| 2005/0202967 A1 | 9/2005 | Hoefer et al. |
| 2005/0245769 A1 | 11/2005 | Kohler et al. |
| 2006/0104877 A1 | 5/2006 | Cadours et al. |
| 2006/0150665 A1 | 7/2006 | Weimer et al. |
| 2006/0197053 A1 | 9/2006 | Shiflett et al. |
| 2006/0251961 A1 | 11/2006 | Olbert et al. |
| 2006/0264645 A1 | 11/2006 | Zhou et al. |
| 2007/0004903 A1 | 1/2007 | Hoff et al. |
| 2007/0095645 A1 | 5/2007 | Masse |
| 2007/0144186 A1 | 6/2007 | Shiflett et al. |
| 2007/0164462 A1 | 7/2007 | Liu et al. |
| 2007/0264180 A1 | 11/2007 | Carrette et al. |
| 2007/0286783 A1 | 12/2007 | Carrette et al. |
| 2008/0028777 A1 | 2/2008 | Boesmann et al. |
| 2008/0114105 A1 | 5/2008 | Hell et al. |
| 2008/0283383 A1 | 11/2008 | Ruffert et al. |
| 2009/0029121 A1 | 1/2009 | Hammermann et al. |
| 2009/0029887 A1 | 1/2009 | Schwab et al. |
| 2009/0036334 A1 | 2/2009 | Schwab et al. |
| 2009/0139232 A1 | 6/2009 | Collis |
| 2009/0170734 A1 | 7/2009 | Schwab et al. |
| 2009/0199709 A1 | 8/2009 | Rojey et al. |
| 2009/0211447 A1 | 8/2009 | Lichtfers et al. |
| 2010/0011958 A1 | 1/2010 | Cadours et al. |
| 2010/0016205 A1 | 1/2010 | Schwab |
| 2010/0029519 A1 | 2/2010 | Schwab et al. |
| 2010/0071557 A1 | 3/2010 | Seiler et al. |
| 2010/0084597 A1 | 4/2010 | Schwab et al. |
| 2010/0086983 A1 | 4/2010 | Gellett et al. |
| 2010/0095703 A1 | 4/2010 | Jork et al. |
| 2010/0104490 A1 | 4/2010 | Bouillon et al. |
| 2010/0132551 A1 | 6/2010 | Bouillon et al. |
| 2010/0186590 A1 | 7/2010 | Vorberg et al. |
| 2010/0192770 A1 | 8/2010 | Andarcia |
| 2010/0269528 A1 | 10/2010 | Gerhard et al. |
| 2010/0288126 A1 | 11/2010 | Agar et al. |
| 2010/0300870 A1 | 12/2010 | Massonne et al. |
| 2010/0326126 A1 | 12/2010 | Seiler et al. |
| 2011/0000236 A1 | 1/2011 | Seiler et al. |
| 2011/0081287 A1 | 4/2011 | Bouillon et al. |
| 2011/0094381 A1 | 4/2011 | Lichtfers et al. |
| 2011/0118504 A1 | 5/2011 | Haas et al. |
| 2011/0135549 A1 | 6/2011 | Lichtfers et al. |
| 2011/0185901 A1 | 8/2011 | Jacquin et al. |
| 2011/0247494 A1 | 10/2011 | Dinnage et al. |
| 2011/0256043 A1 | 10/2011 | Blair et al. |
| 2011/0309295 A1 | 12/2011 | Joh et al. |
| 2012/0011886 A1 | 1/2012 | Shiflett et al. |
| 2012/0017762 A1 | 1/2012 | Seiler et al. |
| 2012/0024756 A1 | 2/2012 | Verma et al. |
| 2012/0080644 A1 | 4/2012 | Seiler et al. |
| 2012/0117991 A1 | 5/2012 | Rached |
| 2012/0186993 A1 | 7/2012 | Huang et al. |
| 2012/0247144 A1 | 10/2012 | Seiler et al. |
| 2012/0308458 A1 | 12/2012 | Seiler et al. |
| 2012/0315366 A1 | 12/2012 | Zehnacher et al. |
| 2013/0011314 A1 | 1/2013 | Porcheron et al. |
| 2013/0023712 A1 | 1/2013 | Porcheron et al. |
| 2013/0031930 A1 | 2/2013 | Seiler et al. |
| 2013/0031931 A1 | 2/2013 | Seiler et al. |
| 2013/0118350 A1 | 5/2013 | Rolker et al. |
| 2013/0133327 A1 | 5/2013 | Milam et al. |
| 2013/0219949 A1 | 8/2013 | Seiler et al. |
| 2013/0247758 A1 | 9/2013 | Seiler et al. |
| 2013/0255496 A1 | 10/2013 | Zhang et al. |
| 2013/0263743 A1 | 10/2013 | Seiler et al. |
| 2013/0319022 A1 | 12/2013 | Becze et al. |
| 2013/0327084 A1 | 12/2013 | Shiflett et al. |
| 2014/0005344 A1 | 1/2014 | Rinker et al. |
| 2014/0090558 A1 | 4/2014 | Rolker et al. |
| 2014/0105801 A1 | 4/2014 | Rolker et al. |
| 2014/0120016 A1 | 5/2014 | Rolker et al. |
| 2014/0127103 A1 | 5/2014 | Qi et al. |
| 2014/0356268 A1 | 12/2014 | Schraven et al. |
| 2014/0360369 A1 | 12/2014 | Schraven et al. |
| 2015/0024106 A1 | 1/2015 | Huller et al. |
| 2015/0024247 A1 | 1/2015 | Lockett et al. |
| 2015/0125373 A1 | 5/2015 | Willy et al. |
| 2015/0175738 A1 | 6/2015 | Willy et al. |
| 2015/0175740 A1 | 6/2015 | Willy et al. |
| 2015/0308720 A1 | 10/2015 | Zehnacker et al. |
| 2015/0321139 A1 | 11/2015 | Schraven et al. |
| 2016/0045857 A1 | 2/2016 | Rolker et al. |
| 2016/0115827 A1 | 4/2016 | Rached |
| 2016/0153318 A1 | 6/2016 | Busse et al. |
| 2016/0175766 A1 | 6/2016 | Zehnacker et al. |
| 2017/0354921 A1 | 12/2017 | Zehnacker et al. |
| 2017/0354922 A1 | 12/2017 | Zehnacker et al. |
| 2017/0354923 A1 | 12/2017 | Zehnacker et al. |
| 2017/0354924 A1 | 12/2017 | Irfan et al. |
| 2017/0355680 A1 | 12/2017 | Wang et al. |
| 2017/0355682 A1 | 12/2017 | Willy et al. |

FOREIGN PATENT DOCUMENTS

| | | |
|---|---|---|
| CN | 102335545 | 2/2012 |
| DE | 400 488 | 8/1924 |
| DE | 633 146 | 7/1936 |
| DE | 737031 | 7/1943 |
| DE | 36 23 680 A1 | 1/1988 |
| DE | 266 799 A1 | 4/1989 |
| DE | 195 11 709 | 10/1996 |
| DE | 103 33 546 | 2/2005 |
| DE | 10 2004 053 167 | 5/2006 |
| DE | 10 2010 001 070 | 7/2011 |
| DE | 10 2010 004 779 | 7/2011 |
| DE | 10 2011 055 859 | 6/2013 |
| DE | 10 2013 010 035 | 12/2014 |
| DE | 10 2014 214 670 | 1/2016 |
| DE | 10 2014 214 674 | 1/2016 |
| DE | 10 2014 214 682 | 1/2016 |
| DE | 10 2014 110190 | 1/2016 |
| DE | 10 2015 212 749 | 1/2017 |
| DE | 10 2016 210 481 | 6/2017 |
| DE | 10 2016 204 928 | 9/2017 |
| DE | 10 2016 204 929 | 9/2017 |
| DE | 10 2016 204 930 | 9/2017 |
| DE | 10 2016 204 931 | 9/2017 |
| DE | 10 2016 204 932 | 9/2017 |

(56) References Cited

FOREIGN PATENT DOCUMENTS

| | | |
|---|---|---|
| DE | 10 2016 204 937 | 9/2017 |
| EP | 0 033 529 A1 | 1/1981 |
| EP | 0 047 967 | 9/1981 |
| EP | 0 079 767 | 5/1983 |
| EP | 0 187 130 | 7/1986 |
| EP | 0 193 327 | 9/1986 |
| EP | 0 302 020 | 2/1989 |
| EP | 0 558 019 | 2/1993 |
| EP | 2 636 715 | 9/2013 |
| FR | 670 497 | 11/1929 |
| FR | 2 900 841 A1 | 11/2007 |
| GB | 1 306 853 | 2/1973 |
| GB | 1 501 195 | 2/1978 |
| GB | 2 047 681 | 12/1980 |
| GB | 2 528 494 | 1/2016 |
| JP | 33-009879 B | 11/1958 |
| JP | 57-191407 | 11/1982 |
| JP | 61-129019 | 6/1986 |
| JP | 62-73055 | 4/1987 |
| JP | 1-134180 | 5/1989 |
| JP | H01-198679 | 8/1989 |
| JP | 2-298767 | 12/1990 |
| JP | 4-268176 | 9/1992 |
| JP | 6-307730 | 11/1994 |
| JP | 7-167521 | 7/1995 |
| JP | 2001-219164 | 8/2001 |
| JP | 2002-047258 | 2/2002 |
| JP | 2004-44945 | 2/2004 |
| JP | 2006-239516 | 9/2006 |
| JP | 2006-282525 | 10/2006 |
| JP | 2010-034301 | 2/2010 |
| JP | 2010-54136 | 3/2010 |
| JP | 2013-051238 | 3/2013 |
| JP | 2013-139425 | 7/2013 |
| RU | 2 101 625 | 1/1998 |
| RU | 2 122 642 | 11/1998 |
| RU | 2 183 003 | 5/2002 |
| WO | WO 93/13367 | 7/1993 |
| WO | WO 00/61698 A1 | 10/2000 |
| WO | WO 2002/016671 | 2/2002 |
| WO | WO 2004/016631 | 2/2004 |
| WO | WO 2004/082809 | 9/2004 |
| WO | WO 2006/012097 | 2/2006 |
| WO | WO 2006/048182 | 5/2006 |
| WO | WO 2007/099041 | 9/2007 |
| WO | WO 2009/032959 | 3/2009 |
| WO | WO 2009/074535 | 6/2009 |
| WO | WO 2009/133059 | 11/2009 |
| WO | WO 2010/037109 | 4/2010 |
| WO | WO 2011/131552 | 10/2011 |
| WO | WO 2012/110987 | 8/2012 |
| WO | WO 2012/150051 | 11/2012 |
| WO | WO 2013/041300 | 3/2013 |
| WO | WO 2013/050230 | 4/2013 |
| WO | WO 2013/050242 | 4/2013 |
| WO | WO 2013/072147 | 5/2013 |
| WO | WO 2015/000637 | 1/2015 |
| WO | WO 2017/005538 | 1/2017 |

OTHER PUBLICATIONS

Lewin, et al., "Molecular Features Associated with Polyamine Modulation of NMDA Receptors," *J. Med. Chem.* 41:988-995 (published online Feb. 1998).
Luo, et al., "Dehumidification performance of [EMIM]BF$_4$," *Applied Thermal Engineering* 31(14-15):2772-2777 (Oct. 2011).
Luo, et al., "Investigation of feasibility of ionic liquids used in solar liquid desiccant air conditioning system," *Solar Energy* 86(9):2781-2724 (Sep. 2012).
Ionische Flüssigkeiten—Polarität and Wechselwirkungen mit silikatischen Oberflächen, Dissertation Technische Universität Chemnitz (Nov. 2011); with English language translation of pp. 14, 24, 39-41, 48-49 and 111; also sections 2.3.3, 3.1.1 and 5.3.
Projekt der Deutschen Bundesstiftung: Gasreinigung mit ionischen Flüssigkeiten Umwelt; Endbericht (Sep. 2009); with English language translation of pp. 18-23 and 90-92.
Satori, et al., "Sterically Hindered Amines for $CO_2$ Removal from Gases," *Ind. Eng. Chem. Fundam.* 22(2):239-249 (accepted Jan. 1983).
Gerald Scott, Develpoments in polymer stabilization-5, Chapter 3: Antioxidant action of sterically hindered amines and related compounds, Shlyapintokh and Ivanor; pp. 41-70, Applied Science Publishers (1982).
Shao & Stangeland, "Amines Used in $CO_2$ Capture—Health and Environmental Impacts," Bellona Report (Sep. 2009).
Ulmann's Encyclopedia of Industrial Chemistry, 5th Edition, vol. 83, "Antioxidants" pp. 91-104 (1985).
Wellner, et al., "Entwässerung ionischer Flüssigkeiten in einem Fallfilmverdampfer," *Chemie Ingenieur Technik* 83(9):1493-1501(Jul. 2011); with complete English language translation.
Yunus, "Gaslöslichkeit in ionischen Flüssigkeiten," IsoSORP Application Note Nr. 4:1-2 (Feb. 2014); with complete English language translation.
Encylopedia of Chemical Process and Design, Ed. John J. McKetta, vol. 32. Marcel Deckker, Inc. (1990) pp. 123-126.
English language translation of the German Search Report for corresponding German application DE 10 2016 210 481.0, filed Jun. 14, 2016.
Kuhlmann, et al., "Imidazolium dialkylphosphates—a class of versatile, halogen-free and hydrolytically stable ionic liquids," *Green Chem.* 9:233-242 (2007).
Li, et al., "Efficient absorption of ammonia with hydroxyl-functionalized ionic liquids," *RCS Adv.* 5:81362-81370 (2015).
Kanakubo, et al., "$CO_2$ solubility in and physical properties for ionic liquid mixtures of 1-butyl-3-methylimidazolium acetate and 1-butyl-3-methylimidazolium bis(trifluoromethanesulfonyl) amide," *Journal of Molecular Liquids* 217:112-119 (2016); available online Feb. 12, 2016.
Krannich, et al., "Characterization of Six Hygroscopic Ionic Liquids with Regard to Their Suitability for Gas Dehydration: Density, Viscosity, Thermal and Oxidative Stability, Vapor Pressure, Diffusion Coefficient, and Activity Coefficient of Water," *Journal of Chemical Engineering & Data* 61:1162-1176 (Feb. 2016).
Kriebel, et al., "Absorption, 2. Design of Systems and Equipment," Ulmann's Encyclopedia of Industrial Chemistry, vol. 1, pp. 75-90 (2008).
Lall-Ramnarine, et al., "Probing the Physical Properties, Synthesis and Cellulose Dissolution Ability of Dialkyl Phosphate Ionic Liquids," *Phosphorous, Sulfur, and Silicon* 190:891-895 (2015).
Lungwitz, Ralf, "Ionische Flüssigkeiten—Polarität und Wechselwirkungen mit silikatischen Oberflächen," Dissertation Technische Universität Chemnitz (Nov. 2011); with English language translation of relevant parts.
English language translation of Mao, et al., "Development and Application of New Technique for Recovery of Low Partial Pressure Carbon Dioxide," *Journal of Chemical Industry & Engineering* 25(3):12-15 (Jun. 2004).
English language translation of Rolker, et al., "Separation of carbon dioxide from flue gases by means of absorption," *Chemie Ingenieur Tecknik* 78(4):416-424 (Jul. 2006).
OECD Guidelines for the Testing of Chemicals, Test No. 104, items 14-19, (adopted May 1981).
Projekt der Deutschen Bundesstiftung: Gasreinigung mit ionischen Flüssigkeiten Umwelt; Endbericht (Sep. 2009); with English language translation of relavant parts.
English language translation of XIAO, "Study on Technique for Recovery of Carbon Dioxide from Flue Gas," *Modern Chemical Industry* 24(5):47-49 (May 2004).
U.S. Appl. No. 15/619,561, filed Jun. 12, 2017, Irfan.
U.S. Appl. No. 15/619,566, filed Jun. 12, 2017, Willy.
U.S. Appl. No. 15/619,567, filed Jun. 12, 2017, Wang.
U.S. Appl. No. 15/619,573, filed Jun. 12, 2017, Zehnacker.
U.S. Appl. No. 15/619,577, filed Jun. 12, 2017, Zehnacker.
U.S. Appl. No. 15/619,584, filed Jun. 12, 2017, Zehnacker.

(56) References Cited

OTHER PUBLICATIONS

English language machine translation of Chinese patent reference CN 102335545 which was cited in Supplemental IDS submitted on Apr. 13, 2017 as document B3.
English language translation of German patent reference DD 266 799 which was cited in an IDS submitted on Apr. 13, 2017 as document B1.
English language machine translation of German patent reference DE 36 23 680 which was cited in an IDS submitted on Apr. 13, 2017 as document B4.
English language machine translation of German patent reference DE 195 11 709 which was cited in an IDS submitted on Apr. 13, 2017 as document B5.
English language machine translation of German patent reference DE 103 33 546 which was cited in an IDS submitted on Apr. 13, 2017 as document B6.
English language machine translation of German patent reference DE 10 2004 053 167 which was cited in an IDS submitted on Apr. 13, 2017 as document B7.
English language machine translation of German patent reference DE 10 2010 004 779 which was cited in a Supplemental IDS submitted on Apr. 13, 2017 as document B5.
English language machine translation of German patent reference DE 10 2011 055 859 which was cited in a Supplemental IDS submitted on Apr. 13, 2017 as document B6.
English language machine translation of European patent reference EP 0 033 529 which was cited in an IDS submitted on Apr. 13, 2017 as document B8.
English language translation of European patent reference EP 2 636 715 which was cited in a Supplemental IDS submitted on Apr. 13, 2017 as document B9.
English language machine translation of French patent reference FR 2 900 841 which was cited in an IDS submitted on Apr. 13, 2017 as document B12.
English language machine translation of Japanese patent reference JP 61-129019 which was cited in an IDS submitted on Apr. 13, 2017 as document B14.
English language machine translation of Japanese patent reference JP 1-134180 which was cited in an IDS submitted on Apr. 13, 2017 as document B16.
English language machine translation of Japanese patent reference JP 2-298767 which was cited in an IDS submitted on Apr. 13, 2017 as document B17.
English language machine translation of Japanese patent reference JP-4-268176 which was cited in an IDS submitted on Apr. 13, 2017 as document B18.
English language machine translation of Japanese patent reference JP 2001-219164 which was cited in an IDS submitted on Apr. 13, 2017 as document B21.
English language machine translation of Japanese patent reference JP 2004-44945 which was cited in an IDS submitted on Apr. 13, 2017 as document B23.
English language machine translation of Russian patent reference RU 2 101 625 which was cited in a Supplemental IDS submitted on Apr. 13, 2017 as document B13.
English language machine translation of Russian patent reference RU 2 183 003 which was cited in a Supplemental IDS submitted on Apr. 13, 2017 as document B14.
English language translation of International patent reference WO 2013/050230 which was cited in a Supplemental IDS submitted on Apr. 13, 2017 as document B22.
English language translation of International patent reference WO 2013/050242 which was cited in a Supplemental IDS submitted on Apr. 13, 2017 as document B23.
"Mutual Solubility of Water and Pyridine Derivatives" by Richard M. Stephenson, *J. Chem. Eng. Data 38*, p. 428-431, (Jul. 1993).
"Review of Organic Functional Groups: Introduction to Medicinal Organic Chemistry" by Thomas L. Lemke, Lippincott Williams & Wilkins, p. 40 (2003).
"Review of Organic Functional Groups: Introduction to Medicinal Organic Chemistry" by Thomas L. Lemke, Lippincott Williams & Wilkins, p. 39 (2003).
Brennecke, et al., "Ionic Liquids: Innovative Fluids for Chemical Processing," *AIChE Journal* 47(11):2384-2389 (Nov. 2001).
Chua, et al., "Improved Thermodynamic Property Fields of LiBr—$H_2O$ Solution," *International Journal of Refrigeration* 23:412-429 (Sep. 2000).
De Lucas, et al., "Vapor Pressures, Densities, and Viscosities of the (Water + Lithium Bromide + Lithium Formate) System and (Water + Lithium Bromide + Potassium Formate) System," *Journal of Chemical and Engineering Data, American Chemical Society, US* 48(1):18-22 (Jan. 2003).
De Lucas, et al., "Absorption of Water Vapor into Working Fluids for Absorption Refrigeration Systems," *Industrial & Engineering Chemistry Research, American Chemical Society, US* 46(1):345-350 (2007); (published online Dec. 2006).
Domanska, et al., Solubility of 1-Alkyl-3-ethylimidazolium-Based Ionic Liquids in Water and 1-Octanol, *J. Chem. Eng. Data* 53:1126-1132 (Apr. 2008).
Galàn, et al., "Solvent Properties of Functionalized Ionic Liquids for $CO_2$ Absorption," *IChemE* 85(A1):31-39 (Jan. 2007).
Glebov, et al., "Experimental Study of Heat Transfer Additive Influence on the Absorption Chiller Performance," *International Journal of Refrigeration* 25:538-545 (Aug. 2002).
Kim, et al., "Surface tension and viscosity of 1-butyl-3-methylimidazolium iodide and 1-butyl-3-methylimidazolium tetrafluoroborate, and solubility of lithium bromide+1-butyl-3-methylimidazolium bromide in water," *Korean J. Chem. Eng.* 23(1):113-116 (Jan. 2006).
Kim, et al., "Performance Evaluation of Absorption Chiller Using $LiBr+H_2N(CH_2)_2OH+H_2O$, $LiBr+HO(CH_2)_3OH+H_2O$, and $LiBr+(HOCH_2CH_2NH+H_2O$ as Working Fluids," *Applied Thermal Engineering* 19:217-225 (Feb. 1999).
Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate—Trifluoroethanol," *Fluid Phase Equilibria* 218:215-220.(Apr. 2004).
Li, et al., "Correlation and Prediction of the Solubility of $CO_2$ and $H_2S$ in an Aqueous Solution of 2-Piperidineethanol and Sulfolane," *Ind. Eng. Chem. Res.* 37:3098-3104 (May 1998).
Liu, et al., The physical properties of aqueous solution of room-temperature ionic liquids based on imidazolium:Database and Evaluation, *J. Mol. Liquids* 140:68-72 (Jan. 2008).
Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).
Perez-Blanco, "A Model of an Ammonia-Water Falling Film Absorber," ASHRAE Transactions vol. 94, pp. 467-483, 1988; Presented at the winter meeting in Dallas Texas of the American Society of Heating, Refrigerating and Air-Conditioning Engineers, Inc. (1988).
Rolker, et al., "Abtrennung von Kohlendioxid aus Rauchgasen mittels Absorption," *Chemie Ingenieur Technik* 78:416-424; with English language abstract attached (Jul. 2006).
Wasserscheid, et al., "Ionic Liquids—New "Solutions" for Transition Metal Catalysis," *Angew. Chem. Int. Ed.* 39:3772-3789 (Nov. 2000).
Wu, et al., "Novel Ionic Liquid Thermal Storage for Solar Thermal Electric Power Systems," *Proceeding of Solar Forum. Solar Energy: The Power to Choose* (Apr. 21-25, 2001).
Yoon, et al., "Cycle Analysis of Air-Cooled Absorption Chiller Using a New Working Solution," *Energy* 24:795-809 (Sep. 1999).
Zhang, et al., "Screening of ionic Liquids to Capture CO2 by COSMO-RS and Experiments," *AIChE Journal* 54(10):2171-2728 (Oct. 2008).
Zhou, The Vapor Surfactant Theory of Absorption and Condensation Enhancement, *Proc. Int. Sorption Heat Pump Conference*, (Sep. 24-27, 2002).
Ziegler, et al., "Heat-Transfer Enhancement by Additives," *International Journal of Refrigeration* 19:301-309 (Jun. 1996).

(56) References Cited

OTHER PUBLICATIONS

Ziegler, et al., "Multi-effect absorption chillers," *Rev. Int. Froid* *16*(5):301-311 (1993).
Ziegler, et al., "Recent developments and future prospects of sorption heat pump systems," *Int. J. Therm. Sci. 38*:191-208 (Mar. 1999).
U.S. Appl. No. 14/124,472, filed Dec. 6, 2013, 2014/0090558 A1, Apr. 3, 2014, Rolker.
U.S. Appl. No. 14/373,350, filed Jul. 19, 2014, 2014/0360369 A1, Dec. 11, 2014, Schraven.
U.S. Appl. No. 14/925,183, filed Oct. 28, 2015, 2016/0045857 A1, Feb. 18, 2016, Rolker.
U.S. Appl. No. 14/973,084, filed Dec. 17, 2015, 2016/0175766 A1, Jun. 23, 2016, Zehnacker.

PROCESS FOR PURIFYING AN IONIC LIQUID

CROSS REFERENCE TO RELATED APPLICATIONS

The present application claims priority under 35 USC § 119 to German application, DE 102016210481.0, filed on Jun. 14, 2016, the contents of which is incorporated herein by reference in its entirety.

FIELD OF THE INVENTION

The invention relates to a process for purifying an ionic liquid comprising dialkylimidazolium ions by means of stripping, wherein water vapour is used at a particular temperature. The process according to the invention is characterized in that the decomposition of the ionic liquid is minimized during the process.

BACKGROUND OF THE INVENTION

In air conditioning systems for the aeration and conditioning of buildings or vehicles, the air generally not only has to be cooled, but also dehumidified since the air to be cooled often has such a high humidity that, upon cooling to the desired temperature, the dew point is fallen below. Hence in conventional air conditioning systems, dehumidification of the air accounts for a large part of electricity consumption.

One option for reducing the electricity consumption of air conditioning systems for buildings is the dehumidification of air by adsorption or absorption of water using a drying medium and regeneration of the drying medium laden with water by heating to a temperature at which the water is desorbed again. Compared to adsorption on a solid adsorbent, the advantage of absorption in a liquid absorption medium is that air dehumidification can be carried out with reduced equipment complexity and with less drying medium and that regeneration of the water-laden drying medium using solar heat is easier to carry out.

The aqueous solutions of lithium bromide, lithium chloride or calcium chloride hitherto employed as liquid absorption media in commercial air conditioning systems have the disadvantage that they are corrosive towards the metallic materials of construction typically employed in air conditioning systems and that they thus necessitate the use of expensive specific materials of construction. These solutions can additionally cause problems due to salt crystallizing out of the absorption medium.

Y. Luo, et al., Appl. Thermal Eng. 31 (2011) 2772-2777, proposes using the ionic liquid 1-ethyl-3-methylimidazolium tetrafluoroborate in place of aqueous solutions of lithium bromide for air dehumidification.

Y. Luo, et al., Solar Energy 86 (2012) 2718-2724, proposes using the ionic liquid 1,3-dimethyimidazolium acetate as an alternative to 1-ethyl-3-methylimidazolium tetrafluoroborate for air dehumidification.

US 2011/0247494 A1 proposes, in paragraph [0145], the use of trimethylammonium acetate or 1-ethyl-3-methylimidazolium acetate as liquid drying agent instead of aqueous lithium chloride solution. Example 3 compares water uptake from humid air for a series of further ionic liquids.

CN 102335545 A describes aqueous solutions of ionic liquids as absorption media for air dehumidification. The ionic liquids can contain the anions $[BF_4]^-$, $[CF_3SO_3]^-$, $[CH_3COO]^-$, $[CF_3COO]^-$, $[C_3F_7COO]^-$, $[(CF_3SO_2)_2N]^-$, $[(CH_3)_2PO_4]^-$, $[C_4F_9SO_3]^-$, $[(C_2F_5SO_2)N]^-$ and $[(CF_3SO_2)_3C]^-$.

Commercially available ionic liquids generally comprise impurities which lead to substances that are odour-intensive or are injurious to health entering the dehumidified air upon dehumidification of air using the ionic liquid. In the desorption of water from ionic liquids which contain a basic anion, such as a carboxylate ion, odour-intensive decomposition products are formed which, in the event of a subsequent use of the ionic liquid for the dehumidification of air, enter the dehumidified air.

The problem was also observed that, in the case of purifying ionic liquids containing dialkylimidazolium ions by conventional purification processes, an at least partial decomposition of these ionic liquids occurs. This is apparent on occurrence of foul-smelling decomposition products in the ionic liquid obtained after the purification step.

The object of the present invention therefore consisted of providing a process for purifying an ionic liquid in which the aforementioned problems are minimized and ideally do not arise.

DETAILED DESCRIPTION OF THE INVENTION

The present invention relates to a process for purifying an ionic liquid of the structure $Q^+A^-$, wherein $Q^+$ is a 1,3-dialkylimidazolium ion, and wherein $A^-$ is selected from the group consisting of dialkyl phosphate, alkyl sulphate, alkyl sulphonate, alkyl carboxylate, chloride, hydrogen sulphate, dihydrogen phosphate, monoalkyl hydrogen phosphate, nitrate, characterized in that the ionic liquid of the structure $Q^+A^-$ is subjected to a stripping with water vapour having a temperature of $\leq 99°$ C.

In a preferred embodiment of the present invention, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of dialkyl phosphate, in which the alkyl groups are each independently $C_1$-$C_{10}$-alkyl groups, alkyl sulphate, in which the alkyl group is a $C_1$-$C_{10}$-alkyl group, alkyl sulphonate, in which the alkyl group is a $C_1$-$C_{10}$-alkyl group, alkyl carboxylate, in which the alkyl group is a $C_1$-$C_{10}$-alkyl group, chloride, hydrogen sulphate, dihydrogen phosphate, monoalkyl hydrogen phosphate, in which the alkyl group is a $C_1$-$C_{10}$-alkyl group and nitrate.

A $C_1$-$C_{10}$-alkyl group is unbranched or branched and preferably an unbranched or branched $C_1$-$C_8$-alkyl group, more preferably an unbranched or branched $C_1$-$C_6$-alkyl group, even more preferably an unbranched or branched $C_1$-$C_4$-alkyl group, which is preferably selected from the group consisting of methyl, ethyl, n-propyl, isopropyl, n-butyl, sec-butyl, tert-butyl, even more preferably selected from the group consisting of methyl, ethyl, n-propyl, n-butyl, more especially preferably selected from the group consisting of methyl and ethyl.

In a more preferred embodiment of the present invention, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of dialkyl phosphate, in which the alkyl groups are each independently $C_1$-$C_{10}$-alkyl groups, alkyl sulphate, in which the alkyl group is a $C_1$-$C_{10}$-alkyl group, alkyl sulphonate, in which the alkyl group is a $C_1$-$C_{10}$-alkyl group, alkyl carboxylate, in which the alkyl group is a $C_1$-$C_{10}$-alkyl group, dihydrogen phosphate, monoalkyl hydrogen phosphate, in which the alkyl group is a $C_1$-$C_{10}$-alkyl group.

In a further preferred embodiment of the present invention, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of dialkyl phosphate, in which the alkyl groups are each independently $C_1$-$C_{10}$-alkyl groups, alkyl sulphate, in which the alkyl group is a $C_1$-$C_{10}$-alkyl group, alkyl sulphonate, in which the alkyl group is a $C_1$-$C_{10}$-alkyl group, alkyl carboxylate, in which the alkyl group is a $C_1$-$C_{10}$-alkyl group.

In an even more preferred embodiment of the present invention, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is dialkyl phosphate, in which the alkyl groups are each independently $C_1$-$C_{10}$-alkyl groups. Even more preferably, $Q^+$ is a 1,3-dialkylimidazolium ion, in which the alkyl groups are each independently unbranched or branched $C_1$-$C_6$-alkyl groups, and $A^-$ is dialkyl phosphate, in which the alkyl groups are each independently unbranched or branched $C_1$-$C_6$-alkyl groups. Still more preferably, $Q^+$ is a 1,3-dialkylimidazolium ion, in which the alkyl groups are each independently unbranched or branched $C_1$-$C_4$-alkyl groups, and $A^-$ is dialkyl phosphate, in which the alkyl groups are each independently unbranched or branched $C_1$-$C_4$-alkyl groups. Still more preferably, $Q^+$ is a 1,3-dialkylimidazolium ion, in which the alkyl groups are each independently methyl or ethyl, and $A^-$ is dialkyl phosphate, in which the alkyl groups are each independently methyl or ethyl. Even more preferably, $Q^+$ is a 1,3-dimethylimidazolium cation or a 1-ethyl-3-methylimidazolium cation, preferably a 1-ethyl-3-methylimidazolium cation, and $A^-$ is diethyl phosphate.

In the process according to the present invention, the ionic liquid of the structure $Q^+A^-$ is subjected to a stripping with water vapour having a temperature of ≤99° C. It has been found, surprisingly, that with this process a particularly mild purification of the ionic liquid is possible and, in particular, the problem of odour-forming substances, which occurs due to the decomposition of the ionic liquids when purified by conventional methods, is avoided.

"Stripping" is a physical separation process known to those skilled in the art which is used in many fields for purifying liquids (described for example in M. Kriebel: "Absorption, 2. Design of Systems and Equipment", Ullmann's Encyclopedia of Industrial Chemistry, Electronic Release, chap. 3, Wiley VCH, Weinheim October 2008). In this case, a gas phase (in the case of the present invention water vapour having a temperature of ≤99° C.) is contacted in countercurrent flow with a phase to be purified. In accordance with the invention, this contacting occurs in particular in a column.

Here, the water vapour has a temperature of ≤99° C., particularly in the range from 10° C. to 90° C., preferably in the range from 10° C. to 70° C., more preferably in the range from 10° C. to 60° C., more preferably in the range from 20° C. to 50° C., and even more preferably in the range from 23° C. to 34° C. The temperature of the water vapour can be adjusted by adjusting an appropriate negative pressure in the column in a routine manner by those skilled in the art.

In the process according to the invention, the ionic liquid of the structure $Q^+A^-$ has, in particular, a temperature which is higher than the temperature of the water vapour used. It has been shown specifically that a particularly efficient purification of the ionic liquid is possible by this means. The temperature of the ionic liquid used is preferably at least 1° C. above the temperature of the water vapour used, more preferably at least 5° C., still more preferably at least 10° C., even more preferably at least 30° C., even more especially preferably at least 56° C.

The purification of the ionic liquid may be improved by enlarging the surface area of the ionic liquid. Preferably, for this purpose, the ionic liquid in the process according to the invention is passed at least partially over a bed of filling materials or over a structured packing. Of suitability for this purpose are all filling materials and structured packings which are known to the person skilled in the art from the prior art for distillations and for absorption processes.

Alternatively, the desorption can take place in a falling film apparatus. Suitable falling film apparatuses are falling film evaporators known from the prior art for distillations.

The experiments which follow are intended to illustrate the invention, but without restricting it thereto.

EXAMPLES

Comparative Examples C1 to C4: Purification of the Ionic Liquid 1-ethyl-3-methylimidazolium Diethylphosphate (EMIM DEP) in a Thin Film Evaporator Several mixtures of EMIM DEP with water were subjected to purification in a thin film evaporator. The EMIM DEP was obtained by reaction of N-methylimidazole and triethyl phosphate by reaction according to WO 2004/016631 A1.

The thin film evaporator, abbreviated to TFE, had a diameter of 50 mm and had a length of 650 mm, which resulted in an overall evaporator surface of ca. 0.1 m². The wiper basket of the evaporator was provided with block wipers composed of PTFE and was driven by a motor via magnetic coupling. The evaporator jacket was heated using a thermostat and dibenzyltoluene ("Marlotherm") as heat transfer medium.

Four purification passes were carried out in which, in each case, an aqueous solution of EMIM DEP with a water content specified in each case below was used. For this purpose, water was firstly added to EMIM DEP with stirring in order to set a defined water content.

The water content of the solutions in the various passes were:

Example C1: 5% by weight; Example C2: 10% by weight; Example C3: 15% by weight;

Example C4: 20% by weight. The % by weight signifies the proportion of water, based on the total aqueous solution of EMIM DEP, which was supplied as feed to the TFE.

The use of aqueous solutions in the comparative experiments with the TFE ensures better comparability of the results with those of the stripping experiments according to the invention in which a certain proportion of the water vapour is always passed into the ionic liquid to be purified.

Before use in the TFE, the aqueous mixtures of EMIM DEP investigated were adjusted to a temperature of 24° C. The feed was then conveyed for the experiments from a storage vessel via a toothed wheel pump into the evaporator at ~2.00 to 2.29 kg/h. The TFE jacket had a temperature of 150° C. There, the water and also a majority of the odour-forming components were evaporated out of the ionic liquid, condensed and collected in a distillate container which had a temperature of 5° C.

The vapour stream formed in the evaporator was condensed by means of an external condenser and the resulting distillate collected in a storage container. The unevaporated portion of the feed ran at the base of the evaporator into a further storage container. The whole system was operated at a negative pressure of 40 mbar by means of a vacuum pump (Vacubrand).

After the experiment, the ionic liquid remaining in the TFE was assessed with respect to the N-methylimidazole content.

The N-methylimidazole impurity is due to the residue content of reactant from the synthesis of the EMIM DEPs investigated but also to decomposition of the EMIM DEP in the TFE. N-Methylimidazole is constantly removed from the EMIM DEP during the purification process in the TFE, but is constantly "replenished" by decomposition of the EMIM DEP during the reaction. The residual content of N-methylimidazole therefore provides information about the extent of EMIM DEP decomposition during the purification process.

For the N-methylimidazole analysis, headspace GC-MS analysis was carried out on the starting material and also on the samples from the individual experimental settings. For this purpose, 0.1 g of the sample were incubated at 70° C. for 20 minutes in a sampler and the composition of the gas phase was analysed by gas chromatography and mass spectrometry.

For the gas chromatography ("GC"), an instrument from Hewlett Packard ("HP 6890") was used (sampler: Turbomatrix 40 from Perkin Elmer). For the mass-spectrometric analysis, an instrument from Hewlett Packard ("HP 5973") was used.

The N-methylimidazole contents determined in the EMIM DEP after carrying out Examples C1 to C4, based on the N-methylimidazole content in the feed, which was set to 100%, were: C1: 12%; C2: 30%; C3: 36%; C4: 40%.

Thus, in the gas phase of the purified EMIM DEP, a high fraction of N-methylimidazole was still detectable. This indicates decomposition of the EMIM DEP in the TFE during the purification.

Inventive Examples I1-I6: Purification of EMIM DEP by Means of Stripping

For the stripping experiments, a glass column (internal diameter 50 mm) was used, which was equipped in total with 2 m of a fabric structure packing (type A3-500) from Montz. The column was composed of two segments each of one meter length. Both segments were equipped with an electrical compensation heater. The EMIM DEP (obtained by reaction of N-methylimidazole and triethyl phosphate according to a reaction according to WO 2004/016631 A1) was fed to the top of the column, where the feed from EMIM DEP was pre-heated to a temperature of ~90° C. Via the feed into the column, two condensers were located at which the stripping vapour was condensed with the stripped components and then was passed from the column via a vapour dome.

The water vapour required for the stripping was generated in a falling-film evaporator in the bottom region of the column. Here, water was pumped into the evaporator by means of a metering pump, fully evaporated there and then passed into the column. The temperature of the stripping vapour was 34° C. The water vapour feed was fed to the column at a mass rate of 0.75 kg/h. At the base of the column a so-called vapour dome was located at which the liquid trickling from above was collected and then was discharged from the column.

To deodorize the ionic liquid in the stripping column, the column was initially heated to a temperature of 95° C. and then adjusted to the operating pressure of 48 mbar. Subsequently the water evaporation was put into operation on the falling film evaporator. Once this was running in stationary fashion, the preheated feed of the ionic liquid EMIM DEP was started at the top of the column. During the operation at the respective settings, the distillate generated on the condenser, consisting of water and the odour-forming components, was discharged into a distillate container. The deodourized ionic liquid was discharged at the base of the column and cooled in so doing.

6 runs, I1-I6, were carried out in which only the amount of feed of ionic liquid was varied at a constant amount of stripping vapour in order to obtain different mass flow ratios of ionic liquid to stripping vapour.

The amount of feed of ionic liquid in the various experiments I1 to I6 was respectively:

I1: 1.3 kg/h; I2: 2.8 kg/h; I3: 3.6 kg/h; I4: 4.8 kg/h; I5: 5.5 kg/h; I6: 7.6 kg/h.

During the experiments, the ionic liquid discharging at the bottom of the column was regularly sampled. The experimental settings were run for 6 h in each case in order to establish steady-state operating conditions.

The ionic liquid discharged at the base of the column (bottoms) was analysed for its water content. The Karl Fischer method was used for the water analysis using a titrator from Mettler (Mettler Toledo DL-38). The water content of the purified ionic liquid EMIM DEP was from 5.0 to 6.2% in all runs I1 to I6. For the samples of the individual experiments I1 to I6 in the stripping column, a headspace GC-MS analysis was carried out (procedure and equipment details see C1 to C4) to be able to assess the content of N-methylimidazole. The analytical results showed that the component N-methylimidazole was no longer detectable in the gas phases from the individual experimental settings, i.e. was far below the values which could be obtained with the TFE.

Accordingly, it is evident from the experiments that purification of an ionic liquid having a dialkylimidazolium ion is possible with the process according to the invention, wherein the decomposition or reverse reaction of this ionic liquid can be suppressed. This is distinctly evident on the basis of the disappearance of the typical N-methylimidazole decomposition product in the gas phase of the EMIM DEP purified by means of stripping. This result was completely surprising.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for purifying an ionic liquid of the structure $Q^+A^-$, wherein $Q^+$ is a 1,3-dialkylimidazolium ion, and wherein $A^-$ is selected from the group consisting of: dialkyl phosphate; alkyl sulphate; alkyl sulphonate; alkyl carboxylate; chloride; hydrogen sulphate; dihydrogen phosphate; monoalkyl hydrogen phosphate; and nitrate;

wherein the ionic liquid of the structure $Q^+A^-$ is subjected to a stripping with water vapour having a temperature of ≤99° C.

2. The process of claim 1, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of:

dialkyl phosphate, in which the alkyl groups are each independently $C_1$-$C_{10}$-alkyl groups; alkyl sulphate, in which the alkyl group is a $C_1$-$C_{10}$-alkyl group; alkyl sulphonate, in which the alkyl group is a $C_1$-$C_{10}$-alkyl group; alkyl carboxylate, in which the alkyl group is a $C_1$-$C_{10}$-alkyl group; chloride; hydrogen sulphate; dihydrogen phosphate; monoalkyl hydrogen phosphate, in which the alkyl group is a $C_1$-$C_{10}$-alkyl group; and nitrate.

3. The process of claim 2, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of: dialkyl phosphate, in which the alkyl groups are each independently $C_1$-$C_{10}$-alkyl groups; alkyl sulphate, in which the alkyl group is a $C_1$-$C_{10}$-alkyl group; alkyl sulphonate, in which the alkyl group is a $C_1$-$C_{10}$-alkyl group; alkyl carboxylate, in which the alkyl group is a $C_1$-$C_{10}$-alkyl group; dihydrogen phosphate; and monoalkyl hydrogen phosphate, in which the alkyl group is a $C_1$-$C_{10}$-alkyl group.

4. The process of claim 3, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is dialkyl phosphate, in which the alkyl groups are each independently $C_1$-$C_{10}$-alkyl groups.

5. The process of claim 4, wherein $Q^+$ is a 1,3-dimethylimidazolium cation or a 1-ethyl-3-methylimidazolium cation.

6. The process of claim 5, wherein $Q^+$ is a 1-ethyl-3-methylimidazolium cation.

7. The process of claim 5, wherein $A^-$ is diethyl phosphate.

8. The process of claim 7, wherein $Q^+$ is a 1-ethyl-3-methylimidazolium cation.

9. The process of claim 1, wherein the water vapour has a temperature in the range of 10° C. to 90° C.

10. The process of claim 1, wherein the structure $Q^+A^-$ has a temperature which is higher than the temperature of the water vapour used.

11. The process of claim 1, wherein the ionic liquid is passed at least partially over a bed of filling materials or over a structured packing.

12. The process of claim 9, wherein the structure $Q^+A^-$ has a temperature which is higher than the temperature of the water vapour used.

13. The process of claim 12, wherein the ionic liquid is passed at least partially over a bed of filling materials or over a structured packing.

14. The process of claim 13, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of: dialkyl phosphate, in which the alkyl groups are each independently $C_1$-$C_{10}$-alkyl groups; alkyl sulphate, in which the alkyl group is a $C_1$-$C_{10}$-alkyl group; alkyl sulphonate, in which the alkyl group is a $C_1$-$C_{10}$-alkyl group; alkyl carboxylate, in which the alkyl group is a $C_1$-$C_{10}$-alkyl group; chloride; hydrogen sulphate; dihydrogen phosphate; monoalkyl hydrogen phosphate, in which the alkyl group is a $C_1$-$C_{10}$-alkyl group; and nitrate.

15. The process of claim 14, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is selected from the group consisting of: dialkyl phosphate, in which the alkyl groups are each independently $C_1$-$C_{10}$-alkyl groups; alkyl sulphate, in which the alkyl group is a $C_1$-$C_{10}$-alkyl group; alkyl sulphonate, in which the alkyl group is a $C_1$-$C_{10}$-alkyl group; alkyl carboxylate, in which the alkyl group is a $C_1$-$C_{10}$-alkyl group; dihydrogen phosphate; and monoalkyl hydrogen phosphate, in which the alkyl group is a $C_1$-$C_{10}$-alkyl group.

16. The process of claim 15, wherein, in the ionic liquid of the structure $Q^+A^-$, $Q^+$ is a 1,3-dialkylimidazolium ion, in which the alkyl groups are each independently $C_1$-$C_{10}$-alkyl groups, and $A^-$ is dialkyl phosphate, in which the alkyl groups are each independently $C_1$-$C_{10}$-alkyl groups.

17. The process of claim 16, wherein $Q^+$ is a 1,3-dimethylimidazolium cation or a 1-ethyl-3-methylimidazolium cation.

18. The process of claim 17, wherein $Q^+$ is a 1-ethyl-3-methylimidazolium cation.

19. The process of claim 17, wherein $A^-$ is diethyl phosphate.

20. The process of claim 19, wherein $Q^+$ is a 1-ethyl-3-methylimidazolium cation.

* * * * *